(12) United States Patent
Kramer et al.

(10) Patent No.: US 7,996,246 B2
(45) Date of Patent: Aug. 9, 2011

(54) NURSING HOME EVALUATION SYSTEM

(75) Inventors: Andrew M. Kramer, Centennial, CO (US); Peter J. Kramer, Centennial, CO (US); Matthew J. Morris, Denver, CO (US); Ian Schreuder, Denver, CO (US)

(73) Assignee: Nursing Home Quality, LLC, Centennial, CO (US)

( * ) Notice: Subject to any disclaimer, the term of this patent is extended or adjusted under 35 U.S.C. 154(b) by 713 days.

(21) Appl. No.: 12/126,033

(22) Filed: May 23, 2008

(65) Prior Publication Data

US 2009/0292558 A1 Nov. 26, 2009

Related U.S. Application Data

(60) Provisional application No. 61/054,724, filed on May 20, 2008.

(51) Int. Cl.
*G06F 19/00* (2006.01)
(52) U.S. Cl. .................. 705/3; 705/2; 702/182
(58) Field of Classification Search ......... 705/2; 702/19
See application file for complete search history.

(56) References Cited

U.S. PATENT DOCUMENTS

| | | | |
|---|---|---|---|
| 7,911,348 B2 * | 3/2011 | Rodgers | 340/573.1 |
| 2002/0019747 A1 * | 2/2002 | Ware et al. | 705/2 |
| 2003/0167187 A1 * | 9/2003 | Bua | 705/2 |
| 2005/0222870 A1 | 10/2005 | Schumann et al. | |
| 2006/0161456 A1 * | 7/2006 | Baker et al. | 705/2 |
| 2008/0058615 A1 | 3/2008 | Clapp et al. | |
| 2008/0059230 A1 * | 3/2008 | Manning et al. | 705/2 |
| 2008/0133141 A1 * | 6/2008 | Frost | 702/19 |
| 2010/0174557 A1 * | 7/2010 | Bundschus et al. | 705/3 |

OTHER PUBLICATIONS

Quality Indicator Survey Surveyor Training Manual, http://replay.waybackmachine.org/20070519001155/http://www.nursinghomequality.com/cms_forms/Training_Manual_Cover_Page.pdf, Retreived May 19th, 2007.*
Rantz et al., "Verifying Nursing Home Care Quality Using Minimum Data Set Quality Indicators and Other Quality Measures," J Nurs Care Q, 1997, vol. 12, No. 2, pp. 54-62.
"What is QIS?, Datasheet [online] Nursing Home Quality", Jan. 12, 2008, retrieved from the Internet on May 29, 2009, URL:http://web.archive.org/web/20080112160957/www.nursinghomequality,com/what_is_gis.htlm, pp. 1-2.

* cited by examiner

*Primary Examiner* — Gerald J. O'Connor
*Assistant Examiner* — Jonathan K Ng
(74) *Attorney, Agent, or Firm* — Marsh Fischmann & Breyfogle LLP; Daniel J. Sherwinter

(57) ABSTRACT

Methods, systems, and devices are described for determining resource allocation in a resident care facility, like a nursing home facility. Embodiments of the invention provide assessment questions to an assessor via a computer interface. The assessment questions may be based on a base assessment model having questions relating to a number of resident care areas. Responses to the assessment questions may be received, some relating to answers provided to the assessor by respondents (e.g., residents or staff of the resident care facility). The responses may be processed to generate an assessment dataset, which may then be used to generate quality scores for the various resident care areas. The quality scores may indicate likelihoods of citation in the resident care areas as a function of data derived from the base assessment model. The quality scores and/or assessment results may then be graphically displayed and used to formulate a resource allocation determination.

42 Claims, 8 Drawing Sheets

NURSING HOME EVALUATION SYSTEM

CROSS REFERENCE

This application claims priority from co-pending U.S. Provisional Patent Application No. 61/054,724, filed on May 20, 2008, entitled "NURSING HOME EVALUATION SYSTEM," which is hereby incorporated by reference in its entirety for all purposes.

Embodiments of the invention relate to resource allocation in general and, in particular, to resource allocation for resident care facilities.

BACKGROUND

Often, government oversight of resident care facilities is used to protect the residents of those facilities from abuse, lack of quality, and other environmental concerns. In certain cases, government oversight programs use government surveyors to gather information from a facility to identify areas of concern. These areas may be further investigated for non-compliance or other undesirable conditions. The investigations may result in issuance of citations to the facility.

While the government oversight programs may collect valuable types of information from resident care facilities, many have argued that certain programs involve large amounts of subjectivity, resulting in citations being issued with little predictability, objectivity, or consistency. Further, many of the government oversight programs provide little useful feedback to the cited facilities, making it difficult for the facilities to improve. Without more information and more predictable results, it may be difficult for facilities to take effective and efficient remedial measures and avoid future citations.

Thus, it may be desirable to provide nursing home managers with access to more information for use in making resource allocation determinations, particularly relating to quality improvements.

SUMMARY

Among other things, methods, systems, and software are described for determining resource allocation in a resident care facility. Embodiments of the invention provide resident care facilities with facility assessment capabilities. One set of facility assessment capabilities provided to the resident care facility may substantially mimic the data collection and analysis of a base assessment model, like a government oversight program. Another set of facility assessment capabilities may provide additional types of data collection and analysis to assist a resident care facility in making resource allocation determinations and/or to avoid citation.

In one embodiment, a method for generating information for determining resource allocation in a nursing home facility is provided. Assessment questions are provided to an assessor via a computer interface, the set of assessment questions being based on the Quality Indicator Survey. The Quality Indicator Survey comprises questions addressing a number of resident care areas relating to choices, dignity, abuse, health, personal property, and quality; and the set of assessment questions relates to at least a portion of the resident care areas comprised in the Quality Indicator Survey. Responses to the assessment questions are received via the computer interface, the responses being based on answers provided to the assessor by respondents. The respondents may include residents of the nursing home facility, relatives of residents, employees of the nursing home facility, or others. Quality scores are generated for each of the resident care areas based on the responses, each quality score being indicative of a likelihood of citation in that resident care area as a function of data derived from the Quality Indicator Survey. Each quality score is graphically displayed in relation to its resident care areas as a function of the data derived from the Quality Indicator Survey. A resource allocation determination is then formulated as a function of the quality scores.

In some other embodiments, a computer-readable storage medium is provided. The computer-readable storage medium has computer-readable code embodied in it for directing operation of a computer, the computer-readable code including instructions for generating information for determining resource allocation in a resident care facility. The instructions are in accordance with the following: providing a set of assessment questions to an assessor via the computer, the set of assessment questions being based on a base assessment model having questions relating to a number of resident care areas; receiving, via the computer, responses to at least a portion of the set of assessment questions, at least a portion of the responses relating to answers provided to the assessor by a set of respondents; processing the responses to generate an assessment dataset; and generating a quality score for at least one of the resident care areas, the quality score being based on the assessment dataset and indicative of a likelihood of citation in the resident care area as a function of data derived from the base assessment model. In certain embodiments, the instructions are further in accordance with displaying the quality score graphically in relation to the data derived from the base assessment model; analyzing the assessment dataset to generate an analytic dataset; or formulating a resource allocation determination as a function of the quality score.

BRIEF DESCRIPTION OF THE DRAWINGS

A further understanding of the nature and advantages of embodiments of the invention may be realized by reference to the following drawings. In the appended figures, similar components or features may have the same reference label. Further, various components of the same type may be distinguished by following the reference label by a dash and a second label, or by a lower-case character, that distinguishes among the similar components. If only the first reference label is used in the specification, the description is applicable to any one of the similar components having the same first reference label irrespective of the second reference label.

DETAILED DESCRIPTION

Figure 1:
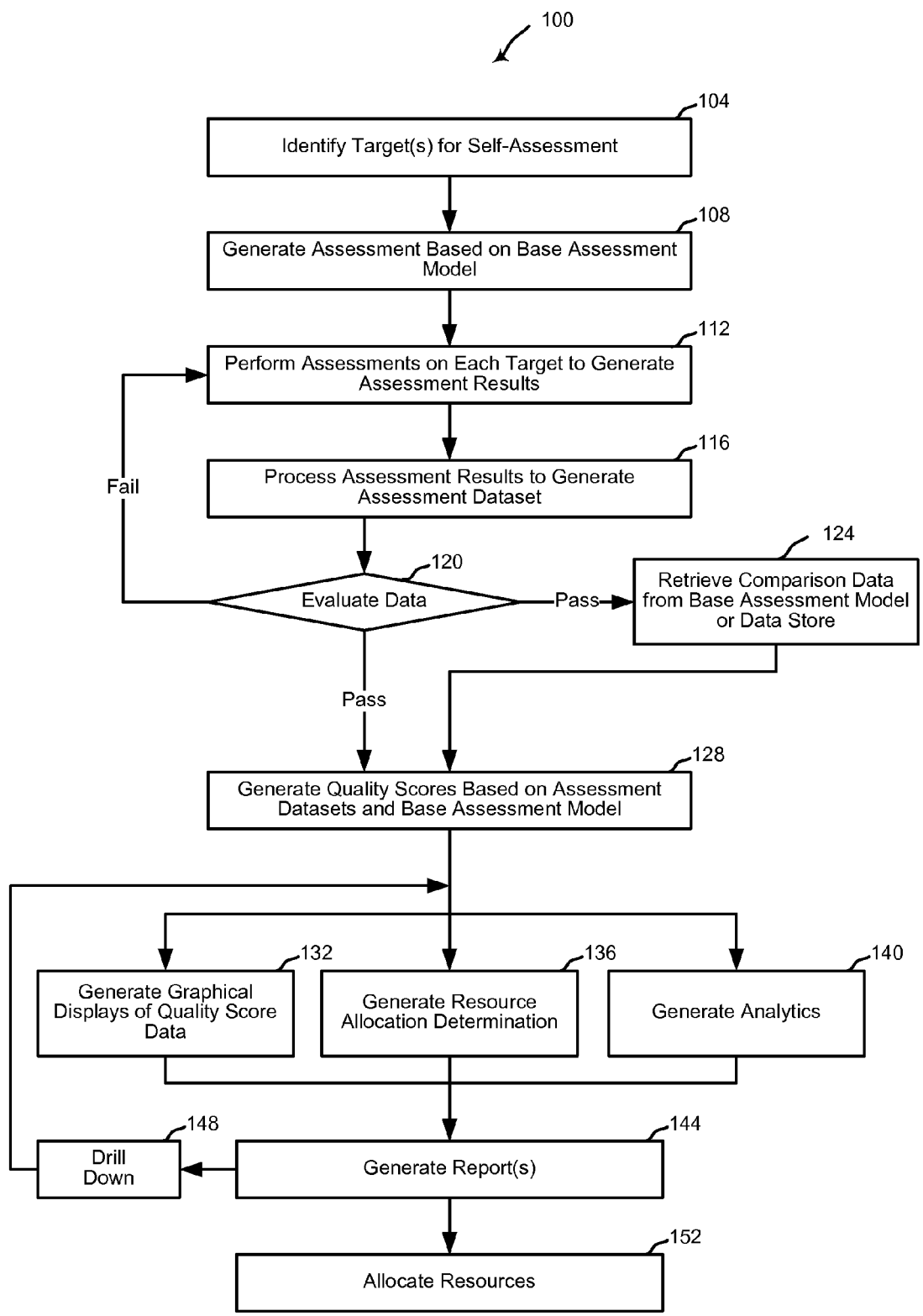
FIG. 1 shows a flow diagram of a method for determining resource allocation in a resident care facility, according to various embodiments of the invention.

Typical examples of government oversight programs for resident care facilities may involve various stages. One stage may provide for the conducting of audits by government regulatory agents to identify areas of potential concern. The audits may include assessments of residents, assessments of resident's relatives and/or friends, assessments of facility staff, assessor observations, and other information collection. Certain audit results in a particular area may trigger another stage, in which a more thorough investigation would be performed into that area (e.g., a "Stage II investigation"). If the more thorough investigation into the area of concern unveils certain negative results (e.g., statutory non-compliances), still another stage may be triggered, in which a citation could be issued against the facility.

Many have argued that much of the oversight process involves large amounts of subjectivity, particularly during the information gathering and analysis processes included in government audits. This subjectivity could result in citations being issued with little predictability, objectivity, or consistency. Without predictable, objective, and consistent results, it may be difficult for facilities to know how to improve their quality and avoid future citations.

In the nursing home industry, for example, most states use a three-stage oversight program, like the one outlined above. Government surveyors may survey a facility to identify care areas of concern. Once identified, a Stage II investigation may be triggered, which may result in a citation. Partly in response to concerns over subjectivity of these oversight programs, the Quality Indicator Survey ("QIS") was developed. The QIS, which claims to be more objective and resident-centered than the traditional oversight models, has been, or is currently being, adopted by a number of states in the United States.

Several aspects of the QIS, however, may limit its effectiveness with respect to nursing home managers (e.g., boards, managers, supervisors, etc.). One such aspect of the QIS is the lack of information available to the nursing home managers after an audit. For example, while nursing home managers may be notified of failures (e.g., citations) in certain care areas, they may not be provided with enough information to determine the root causes of the citations, areas for improvement, etc. Another such aspect is the fact that nursing home managers may have to wait for an audit to find out whether and where improvements are needed. For example, there may be no way for a nursing home manager to proactively predict areas where the nursing home may be audited.

For at least these reasons, it may be difficult for nursing home managers to determine how best to allocate resources. For example, a manager of a large conglomerate may focus on improving food choices for its residents after receiving complaints, while being unaware of a large occurrence of pressure ulcers among residents of a particular wing of a particular facility. Currently, the nursing home may continue to be unaware of the problem until receiving a citation; and even then, the nursing home manager may be provided with too little information to optimally address the cause of problem.

Among other things, methods, systems, and software are described for determining resource allocation in resident care facilities. Throughout the specification, embodiments of the invention will be described with reference to nursing home facilities. It will be appreciated, however, that, in addition to nursing home facilities, resident care facilities may include orphanages, mental health facilities, hospitals, prisons, or any other facility where residents must be cared for by the staff of the facility.

FIG. 1 shows a flow diagram of a method for determining resource allocation in a resident care facility, according to various embodiments of the invention. The method 100 begins when a nursing home decides to perform a facility assessment. In one case, the nursing home makes this determination as a result of a self-imposed facility assessment schedule. For example, a nursing home's management may decide to self-assess all or part of the nursing home facility each month. In another case, the facility assessment may be dictated by a statutory mandate. For example, a government regulation may mandate certain types and/or frequencies of facility assessment to satisfy certain statutory compliance. In yet another case, the nursing home may be forced or encouraged to perform one or more facility assessments by a third party. For example, a legal authority may mandate facility assessments as part of a citation or a lawsuit. In any of these or other cases, the nursing home may begin at block 104 by identifying the target or targets of the facility assessment. For example, a nursing home may opt to perform a facility assessment only on part of its facility (e.g., one wing or one floor), a portion of its patients (e.g., patients with certain conditions or those identified in prior facility assessments), a portion of its properties (e.g., one of many nursing homes owned or operated by a single conglomerate), etc.

Before or after a target has been identified at block 104, an assessment may be generated at block 108 based on a base assessment model. In some embodiments, the generated assessment is the same, regardless of the target or targets identified. In other embodiments, the assessment is generated differently depending on a number of criteria. For example, the assessment may be generated with particular types of questions directed toward a certain medical condition of a target group of residents. In still other embodiments, the assessment is generated with particular questions based on the types of assessment being performed. For example, assessment questions and/or formats may be tailored to interviewing residents of the facility, interviewing relatives or friends of residents of the facility, interviewing staff of the facility, recording personal observations of the assessor regarding residents or aspects of the facility, reviewing census sample records, reviewing admission records, or any other useful type of information gathering.

Embodiments of the assessments generated at block 108 are based on a base assessment model. In certain embodiments, the base assessment model includes questions, question formats, and other information; while in other embodiments, the base assessment model includes information from which assessment questions may be derived. Some embodiments of the base assessment model include information taken or derived from a government assessment program. Some assessment programs may use certain measures to determine characteristics of a resident care facility. For example, a traditional government survey model for nursing home facilities may include a Minimum Data Set, having various quality measures and quality indicators in thirty resident care area categories. Different types of measures in the base assessment model may be used for different reasons. For example, the quality measures and quality indicators may help point to areas of concern, which may warrant further investigation. Further, some types of measures are risk adjusted, such that certain measures may only apply to or may have different sensitivities for certain resident groups. For example, a measure relating to incontinence may be evaluated differently (e.g., may be given more weight) for high risk residents than for low risk residents.

In one embodiment, the base assessment model includes the QIS. The QIS may include questions relating to a large number of resident care areas and resident care sub-areas. For example, the resident care areas may include choices, dignity, abuse, health, personal property, quality, and others. Resident care sub-areas in the resident care area of choices, for example, may be choice of activities, choice of food, etc. In some cases, questions may relate to a single resident care area or sub-area, while in other cases, questions may simultaneously relate to multiple resident care areas or sub-areas.

In some embodiments, the base assessment model may include other information for use in generating the assessment. In certain embodiments, resident care facilities and/or other entities may add information to the base assessment model to influence future assessments. For example, a nursing home may add certain questions to identify where a resident resides within the nursing home facility (e.g., which floor), or how residents are responding to certain initiatives established by the nursing home. Other embodiments of the base assessment model may include information from other assessment models, information from past assessments, information relating to previous assessments and/or citations, or any other useful information.

Once the assessment has been generated at block 108, each target may be assessed in block 112 to generate assessment results. The assessment results may include answers to assessment questions, typically in some raw format. For example, a question may seek a yes or no answer by providing a selectable radio button on a graphical user interface ("GUI"). When the "NO" radio button is selected, the GUI may set a flag to "0," and when the "YES" radio button is selected, the GUI may set a flag to "1." The assessment results may simply include a "0" or "1" for that question. In some embodiments, the assessment results are stored in a flat data structure (e.g., in a flat file database), while in other embodiments, the assessment results are stored in a relational data structure (e.g., in a relational database with various dimensional attributes).

Embodiments of the method 100 may process the assessment results in block 116 to generate one or more assessment datasets. In some embodiments, the assessment dataset consists of processed versions of the assessment results (e.g., the answers to the assessment questions). For example, the assessment dataset may include a relational database of assessment results, configured to be data mined (e.g., filtered, sorted, searched, etc.). In other embodiments, the assessment dataset includes other information relating to the assessment. For example, the assessment dataset may include time information (e.g., how long the assessment took to conduct, at what time and on what date the assessment was conducted, etc.), assessor information (e.g., the assessor's name and other identifiers or qualifiers), facility information (e.g., an identifier for the facility within a conglomerate, a location identifier within the facility, the age, location, size, or another characteristic of the facility, etc.), file information (e.g., file type, file size, file name, etc.), or any other useful assessment-related information. It will be appreciated that, where multiple targets are assessed, it may be necessary or desirable to generate multiple assessment datasets. Where multiple assessment datasets are generated, the different assessment datasets may include different types of information or have other different characteristics.

In certain embodiments, the assessment results and/or the assessment dataset are evaluated for one or more reasons at block 120. In one embodiment, the assessment results are evaluated to determine whether the data is in a proper format, whether some or all of the questions have been answered, whether the data has been properly stored and/or uploaded to a server, or any other data auditing function. In another embodiment, certain data goals are set (e.g., a certain number of residents to sample), and the assessment dataset is evaluated to determine whether the data goals have been met. In certain embodiments, where the evaluation in block 120 fails, it may be desirable to perform additional assessments or choose new targets to supplement or supplant assessment data that has already been collected.

In some embodiments, the survey dataset is used in block 128 to generate one or more quality scores. In certain embodiments, each quality score relates to a resident care area, a resident care sub-area, or some combination thereof. In one embodiment, a quality score provides an indication of a level of quality from one to one-hundred, as determined by a set of assessment questions relating to a particular resident care area in an assessed resident care facility. For example, in an assessment, thirty residents are asked a set of assessment questions relating to choices, and only three residents give negative responses. An illustrative quality score may be calculated by:

$$\text{Quality Score} = 100 - \left(\frac{\text{Negative results}}{\text{Total results}} * 100\right) = 100 - \left(\frac{3}{30} * 100\right) = 90.$$

It will be appreciated that many ways are possible for calculating a quality score according to embodiments of the invention. For example, the calculation may be based on positive results, combinations of results, or more complex algorithms (e.g., statistical processing, etc.). In some embodiments, comparison data is retrieved in block 124, which may affect the calculation of quality scores in block 128. The comparison data may provide baseline or normalization information for the quality score calculation, or additional data to make the calculation more precise or useful. In certain embodiments, the comparison data is derived from the base assessment model, while in other embodiments, the comparison data is derived from another source of stored data. In one embodiment, the quality score calculation may depend on statutory information stored as part of the base assessment model. In another embodiment, past assessment results or assessment datasets from past assessments may be used to calculate or refine the calculation of quality scores. For example, the comparison data may include assessment results and/or datasets from past assessments of the same or a different resident care facility, the same or a different sample or geographic location within a resident care facility, the same or a different assessor, etc.

Various embodiments of the method 100 provide different types of functionality for using the quality scores generated in block 128. In some embodiment, the quality scores may be graphically displayed in block 132. It will be appreciated that there are many ways to graphically display data, including using bar charts, histograms, line graphs, pie charts, etc. One embodiment of a method for graphically displaying the quality score data is shown in FIG. 2.

Figure 2:
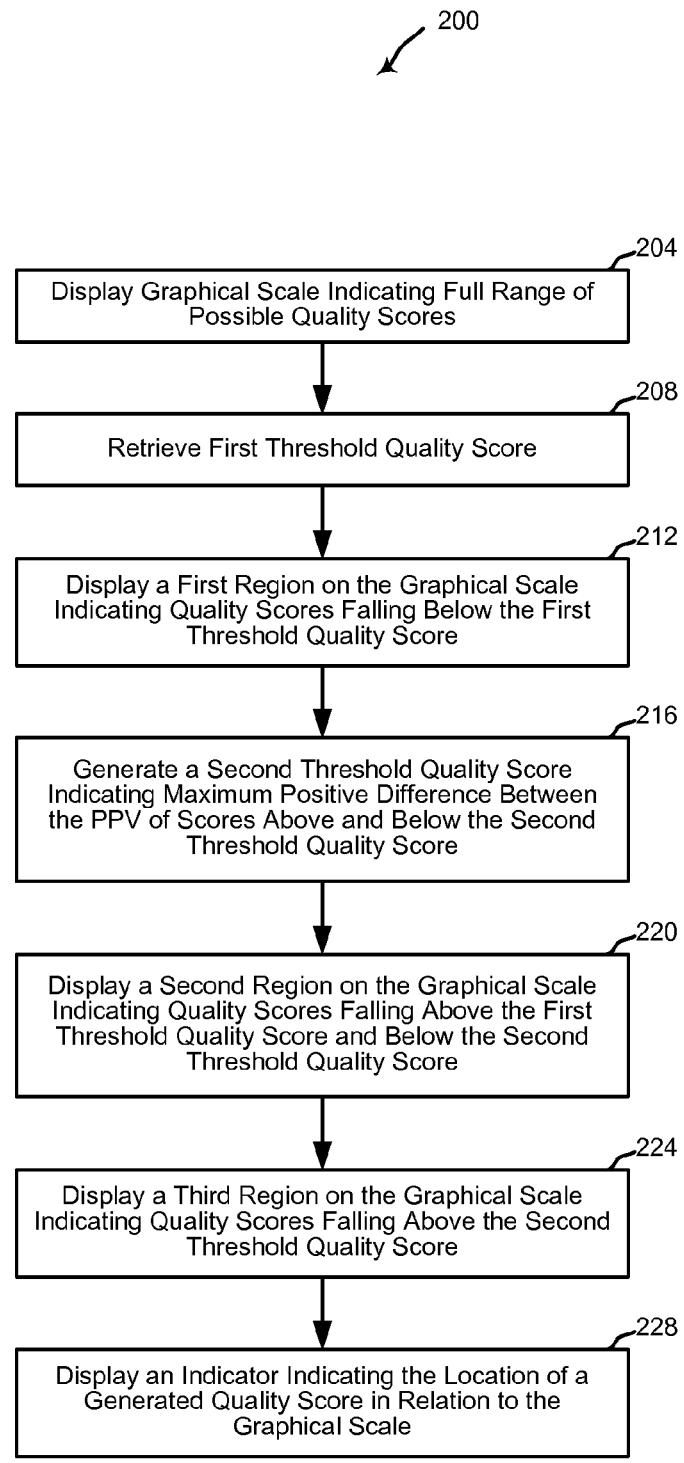
FIG. 2 shows an embodiment of a method for graphically displaying quality score data, according to various embodiments of the invention.

The method 200 in FIG. 2 begins at block 204 by displaying a graphical scale indicating the full range of possible quality scores. For example, the graphical scale may indicate that the quality scores range from one to one-hundred. Further, in certain cases, the graphical scale may also be linear or non-linear, and may include indicia of one or more points on the scale (e.g., a hash mark to indicate intervals of ten quality points).

At block 208, a first threshold quality score is received. In some embodiments, the first threshold quality score is derived from the base assessment model. For example, the QIS may indicate that government surveyors must perform a Stage II investigation into a resident care area, whenever the quality score is less than a particular mandated threshold number. These mandated threshold numbers may be included in the base assessment model, when the base assessment model includes the QIS. For example, the base assessment model may dictate that the first threshold quality score in the "choices" resident care area is forty-seven, a number which may be derived from or equal to the mandated threshold number for that resident care area. It is worth noting that the generated quality scores (e.g., those generated in block 128 of FIG. 1) may not directly correlate to similar types of values in the base assessment model (e.g., the scales may be different or inverted, or may record different numbers of significant digits). As such, it may be necessary or desirable to normalize, or otherwise adjust the values for them to correlate appropriately.

In other embodiments, the first threshold quality score is derived from calculations relating to positive predictive value ("PPV"). For example, in some government oversight programs, the assessment data (e.g., survey data) may be collected to determine where it would be most cost-effective to perform a further investigation (e.g., a Stage II investigation). This determination may include an evaluation of the probability of issuing a citation in an area (e.g., finding non-compliance) as a result of the further investigation. As such, it may be desirable to determine which quality scores in a particular resident care area result in citations and how often. Using this data, it may be possible to calculate the PPV of certain quality scores, e.g., the probability that a given quality score in that resident care area will result in a citation in that care area. PPVs of various possible quality scores may then be determined (e.g., by looking at data from the base assessment model or other comparison data). In one embodiment, these PPVs are evaluated to determine which of the possible quality scores yields (or would yield) the largest PPV for issuing a citation after a Stage II investigation.

It will be appreciated that, depending on the amount and type of available data, it may not be possible to calculate PPVs for all possible quality scores in a given resident care area or sub-area. As such, it may be desirable to interpolate, extrapolate, or otherwise generate data for those scores (e.g., statistically). Similarly, it is worth noting that quality score data may not exist in a base assessment model for all the data collected during a facility assessment. For example, the assessment may generate quality scores for resident care sub-areas, while the base assessment model may only include mandated threshold numbers for resident care areas. In these and other cases, it may be desirable to generate threshold numbers for use as first threshold quality scores. In one embodiment, the first threshold quality score derived for a resident care area is applied as the first threshold quality score for all its resident care sub-areas. In other embodiments, data from the base assessment model and/or the comparison data is used to calculate the first threshold quality score for resident care sub-areas (e.g., by finding PPVs, as discussed above).

In some embodiments, it may be desirable to graphically display regions with respect to the graphical scale displayed at block 204. At block 212, a first region may be displayed, indicating the range of possible quality scores falling below the first threshold quality score, in relation to the graphical scale. In certain embodiments, the first region may indicate a range of quality scores, which, if received from the base assessment model (e.g., from a government survey), would carry a substantially high likelihood of some follow-on action (e.g., a further investigation or a citation). In one embodiment, the first region indicates the range of quality scores for a particular resident care area that would automatically trigger a Stage II investigation if received from QIS results.

In some embodiments of the method 200, an upper region is displayed, indicating the range of possible quality scores falling above the first threshold quality score, in relation to the graphical scale. In certain embodiments, the upper region indicates the range of possible quality scores falling above the first threshold quality score, but below a second threshold quality score. The second threshold quality score may be calculated in block 216 in any useful way, depending on the type of information desired. In one embodiment, the second threshold quality score is calculated using the PPVs of the various possible quality scores for a particular resident care area or sub-area. For example, PPVs may be evaluated to determine a second threshold quality score that would yield the greatest positive difference between the sum of all PPVs of scores within the upper region falling above the second threshold quality score and the sum of all PPVs of scores within the upper region falling below the first threshold quality score.

After generating the second threshold quality score in block 216, it may be desirable to display regions relating to the second threshold quality score. In some embodiments, a second region is displayed in block 220, indicating the range of possible quality scores falling above the first threshold quality score and below the second threshold quality score, in relation to the graphical scale. Further, in some embodiments, a third region is displayed in block 224, indicating the range of possible quality scores falling above the second threshold quality score, in relation to the graphical scale. In one embodiment, the second region indicates the range of quality scores for a particular resident care area that carry a reasonable likelihood of triggering a Stage II investigation if received from QIS results; while the third region indicates the range of quality scores for the particular resident care area that are substantially unlikely to trigger a Stage II investigation if received from QIS results.

Embodiments of the method 200 display an indicator at block 228, indicating the location of the quality score for a particular resident care area or sub-area that was generated from the facility assessment (e.g., in block 128 of FIG. 1). In certain embodiments, the indicator is displayed in relation to the graphical scale and/or the displayed regions. It will be appreciated that there are many ways to display the graphical scale, the various regions, and/or the indicators. Further, it will be appreciated that various other types of labels, indicia, and/or other elements may be included to enhance or adapt the display for various reasons. For example, each region may be color-coded for enhanced viewing.

Figure 3A:
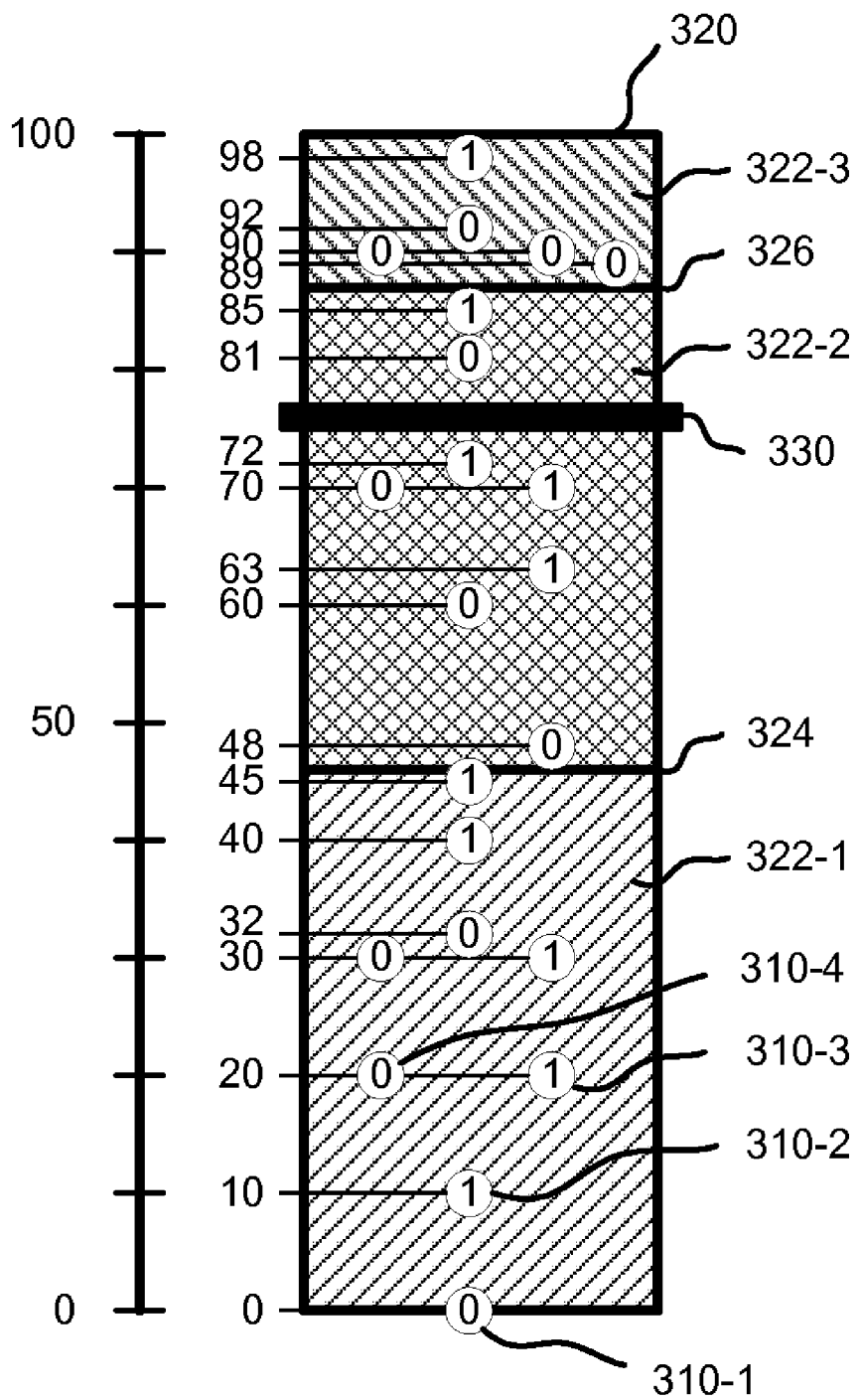
FIG. 3A shows an illustrative graphical display of a quality score for a resident area, according to various embodiments of the invention.

FIG. 3A shows an illustrative graphical display of a quality score for a resident area, according to various embodiments of the invention. A graphical scale 320 is displayed, indicating all possible quality scores for the resident care area of "abuse." The graphical scale 320 includes a first region 322-1, a second region 322-2, and a third region 322-3. The first threshold quality score is displayed as a first boundary 324 between the first region 322-1 and the second region 322-2, and the second threshold quality score is displayed as a second boundary 326 between the second region 322-2 and the third region 322-3.

For illustrative purposes, FIG. 3A shows example data derived from comparison data for the "abuse" resident care area. Each data point 310 indicates a quality score received from the results of a QIS assessment, and whether a citation ultimately resulted (i.e., a "1" indicates that a citation resulted, and a "0" indicates that no citation resulted). For example, a first data point 310-1 indicates that a quality score of zero resulted in no citation; a second data point 310-2 indicates that a quality score of ten resulted in a citation; and a third data point 310-3 and a fourth data point 310-4 indicate that a quality score of twenty resulted in a citation in one instance and no citation in another instance, respectively.

The first boundary 324 (i.e., the boundary between the first region 322-1 and the second region 322-2) may correspond to the threshold measure in the QIS base assessment model for triggering a Stage II investigation into the "abuse" resident care area. In the illustrated embodiment, the first boundary 324 is set at a point that maximizes the PPV of the Stage II investigation trigger. An illustrative graphical derivation of the first boundary 324 is shown in FIG. 3B.

Figure 3B:
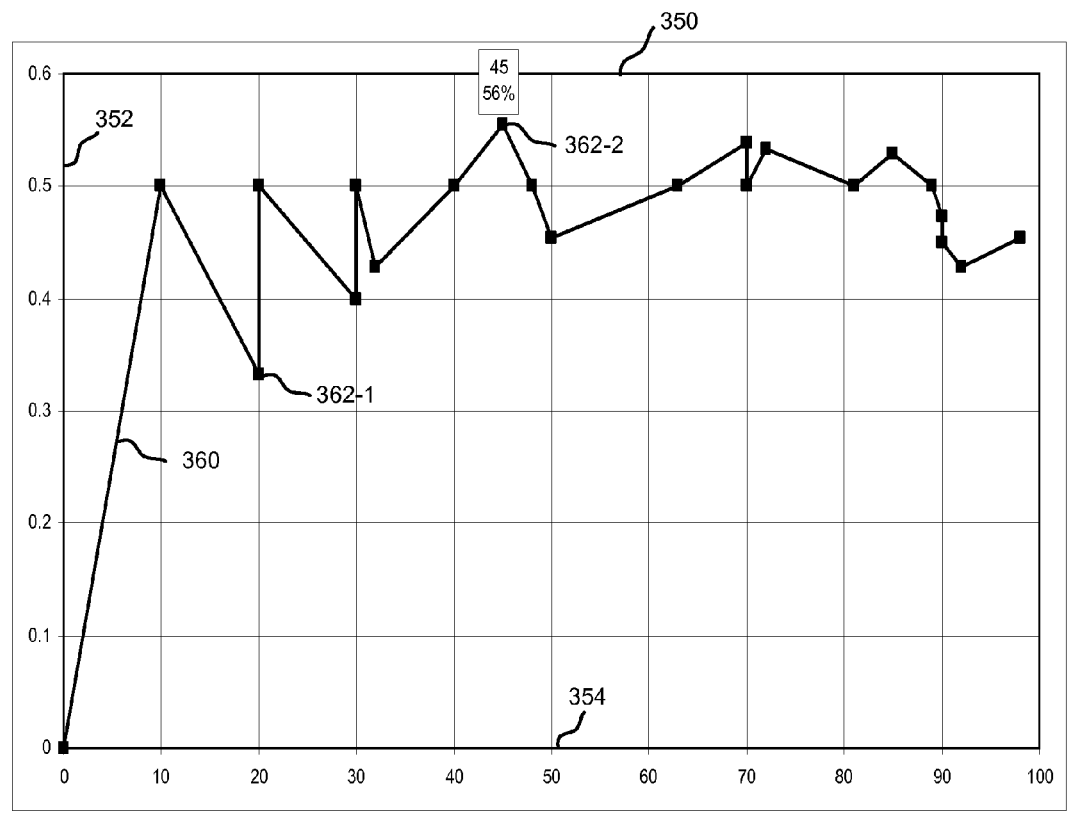
FIG. 3B shows an illustrative graphical derivation of the first boundary, according to various embodiments of the invention.

FIG. 3B shows a graph of average PPVs for each of a series of quality scores derived from a base assessment model, according to the data shown in FIG. 3A. The graph 350 shows average PPV data 360 according to a PPV axis 352 versus a quality score axis 354. The graph 350 further shows an average PPV data point 362, derived at each data point 310 provided in FIG. 3A.

In this illustrative embodiment, the average PPV data points 362 are calculated for each quality score by averaging the PPV data for that quality score with the PPV of all the quality scores below it. For example, at the fourth data point 310-4 of FIG. 3A, the average PPV may be calculated by averaging the data from the first data point 310-1, the second data point 310-2, the third data point 310-3, and the fourth data point 310-4. As discussed above, these data may yield results of "0," "1," "1," and "0," respectively, which averages to an average PPV of 0.5. This average PPV may indicate that, according to past data, a quality score between zero and twenty (i.e., the quality score corresponding to the fourth data point 310-4) carries an approximately fifty-percent chance of yielding a citation in the "abuse" resident care area.

It is worth noting that the maximum average PPV, according to FIG. 3B is around fifty-six-percent, corresponding to a quality score of forty-five (i.e., the second average PPV data point 362-2). In some embodiment, the first boundary 324 in FIG. 3A would then be set to forty-five, corresponding to this maximum average PPV. In other embodiments, the first boundary 324 is set to a different value close to the maximum average PPV. For example, the first boundary 324 is set in FIG. 3A to approximately forty-six, slightly higher than the maximum average PPV. Setting the first boundary 324 in this location may indicate that that there is approximately a fifty-six-percent chance that a nursing home facility that triggers a Stage II investigation under the QIS for the "abuse" resident care area will ultimately be issued a citation for that resident care area.

It is worth noting that the calculation of average PPV in some embodiments is more complex for one or more reasons. In some embodiments, the correlation between quality scores and citations for a resident care area are influenced by data from multiple resident care areas (e.g., where some questions or some information overlaps) or from different types of assessments. For example, portions of the "abuse" resident care area may be investigated in resident interviews, assessor observations, and family interviews. In these cases, an overall likelihood of citation may be calculated as a function of the union of various corresponding PPVs.

Figure 3C:
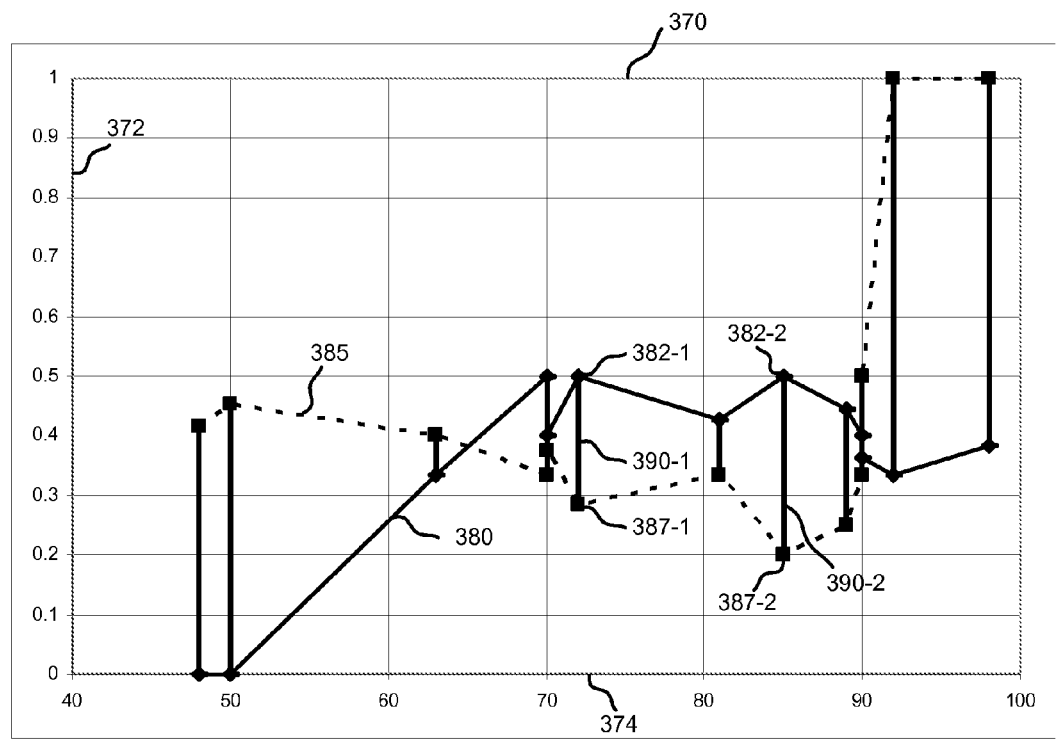
FIG. 3C shows an illustrative graphical derivation of the second boundary, according to various embodiments of the invention.

In some embodiments of the graphical scale 300 of FIG. 3A, the second boundary 324 is determined by attempting to maximize the positive difference between the average PPV of the second region 322-2 and the average PPV of the third region 322-3. An illustrative graphical derivation of the second boundary 324 is shown in FIG. 3C. FIG. 3C shows a graph of average PPVs for each of a series of quality scores, according to the data above the first boundary 324 shown in FIG. 3A.

The graph 370 shows data according to a PPV axis 372 versus a quality score axis 374. A first data series 380 is shown on the graph 370, and includes a first series average PPV data point 382 at each data point 310 provided in FIG. 3A that exceeds the first boundary 324. Each of the first series average PPV data points 382 indicates the average PPV for the data points 310 from the first data point 310 above the first boundary 324 (i.e., at a quality score of forty-eight, in this illustrative case) to the data point 310 correlating to the first series average PPV data point 382. For example, the sixth first series average PPV data point 382-1 indicates an average PPV of around fifty percent for quality scores ranging from forty-eight to seventy-two.

A second data series 385 is shown on the graph 370, and includes a second series average PPV data point 387 at each data point 310 provided in FIG. 3A that exceeds the first boundary 324. Each of the second series average PPV data points 382 indicates the average PPV for the data points 310 from the data point 310 correlating to the second series average PPV data point 387 to the highest available data point 310 (i.e., at a quality score of ninety-eight, in this illustrative case). For example, the sixth second series average PPV data point 387-1 indicates an average PPV of around twenty-nine percent for quality scores ranging from seventy-two to ninety-eight.

The graph 370 further illustrates difference bars 390 at each data point 310 provided in FIG. 3A that exceeds the first boundary 324. Each difference bar 390 indicates the difference, for each data point 310, between the corresponding first series average PPV data point 382 and the corresponding second series average PPV data point 387. The largest positive value of this difference may indicate a location at which there is a substantial difference in PPV between quality scores above the difference and those below the difference. As such, in some embodiments, the second boundary 326 is set at or near the data point 310 having the largest positive average PPV difference.

In this illustrative embodiment, the average PPV at the eighth first series average PPV data point 382-2 (i.e., corresponding to a quality score of eighty-five) may be calculated again as approximately fifty-percent, but the average PPV at the eighth second series average PPV data point 387-2 may be calculated as approximately twenty percent. As such, the eighth difference bar 390-2 indicates a positive average PPV difference of approximately twenty percent, which may be the largest positive value of all the difference bars 390. It is worth noting that the second boundary 326 in FIG. 3A is set slightly above the corresponding location on the graphical scale 320, at approximately eight-seven.

In some embodiments of the graphical scale 300 of FIG. 3A, an indicator 330 is shown, indicating the quality score generated from the facility assessment for the resident care area. As illustrated, the indicator 330 indicates a generated quality score of approximately seventy-six for the "abuse" resident care area. According to the elements of the graphical scale 300, it may be clear that the indicator 330 falls within the second region 322-2. As such, the indicator 330 may indicate that, if a QIS assessment were performed at the nursing home facility at this time, there would be some likelihood, though not a substantially high likelihood, that any investigation into the resident care area of "abuse" would result in a citation in that area.

Returning to FIG. 1, embodiments of the method 100 provide different types of functionality in addition to graphically displaying quality scores, as in block 132. In some embodiments, the quality scores are used to make a resource allocation determination in block 136. The resource allocation may include the allocation of financial resources, staff resources, time, and/or any other types of resources. In some embodiments, resource allocation determinations are made among various resident care areas within a single resident care facility. Other embodiments provide for many other types of resource allocation determinations. In one embodiment, information is used to determine resource allocations among various sections (e.g., wings, cell blocks, departments, etc.) of a resident care facility. In another embodiment, information is used by managers of multiple resident care facilities (e.g., franchises, subsidiaries, conglomerates, etc.) to determine resource allocations among the various resident care facilities. For example, resource allocation determinations may be made by geographic location, facility size, facility type, on a per-facility basis, or in any other useful way.

In some embodiments, the resource allocation determination may be generated in block 136 completely or partially by human analysis of assessment data, for example, including the quality scores generated in block 128. In other embodiments, all or part of the resource allocation determination is generated automatically (e.g., by computer). It will be appreciated that the resource allocation determination may involve a number of factors, which may or may not be directly associated with the assessment data. For example, resource allocation determinations may be influenced by time of year, company goodwill, financial conditions, access to particular resources (e.g., specially trained staff), internal or external pressure (e.g., from a board of directors or a particular group of residents), etc.

Some embodiments of the method 100 may provide functionality to generate certain analytics from the assessment data, for example, including the quality scores, in block 140. The analytics generated in block 140 may include any useful type of data processing. For example, the analytics may include database analysis functions (e.g., sorting, filtering, parsing, etc.) or statistical processing functions (e.g., Bayesian analyses, correlations, line fitting, predictive algorithms, interpolation and extrapolation, etc.). In certain embodiments, the analytics generated in block 140 may be used to generate a resource allocation determination, as in block 136.

In various embodiments of the method 100, reports are generated in block 144. It may be desirable to generate one or more different types of reports for many different reasons. In certain embodiments, report generation may include formatting generated data for output. For example, some or all of the data generated in blocks 112, 116, 120, 124, 128, 132, 136, and/or 140 may be formatted for output as a file, for printing, for uploading to the Internet, or for any other useful type of reporting.

Figure 4:
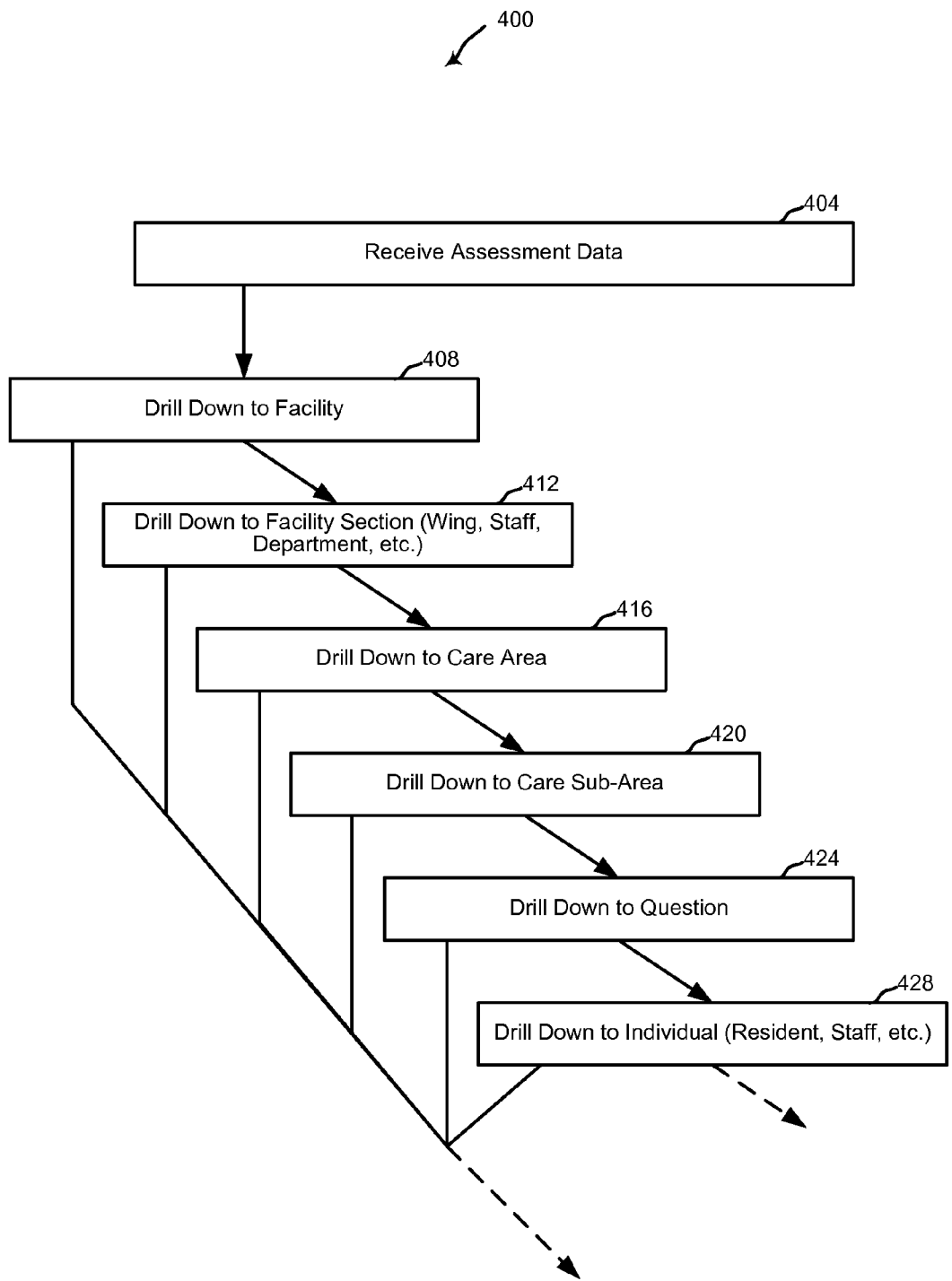
FIG. 4 shows an illustrative flow diagram of drill down functionality, according to various embodiments of the invention.

In some embodiments, the method may provide functionality to drill down to various levels of data in block 148. FIG. 4 shows an illustrative flow diagram of drill down functionality, according to various embodiments of the invention. The method 400 begins in block 404 by receiving assessment data. The assessment data may be any data generated or used in relation to the facility assessment, including, for example, data from blocks 112, 116, 120, 124, 128, 132, 136, and/or 140 of FIG. 1.

Once the assessment data has been generated and/or received, it may be desirable to use the data in a number of different ways. Some of those data uses may be effectuated or enhanced by providing the ability to drill down to different levels of data. Drilling down may include using one or more data processing functions (e.g., sorting, filtering, statistical processing, etc.) to allow viewing and/or analysis of certain portions of the data having certain characteristics. In some embodiments, the method 400 provides functionality to drill down to the facility level in block 408 (e.g., to look at one facility in comparison to other facilities within a conglomerate, competing facilities, average facilities, baseline facilities, etc.), to the facility section level in block 412 (e.g., to be able to compare sections of a particular facility by wing, property, floor, department, staff group, resident group, specialty, etc.), to the resident care area level in block 416 (e.g., to be able to compare how a facility is performing in certain resident care areas versus other resident care areas, etc.), to the resident care sub-area level in block 420 (e.g., to be able to compare how a facility is performing in certain resident care sub-areas versus other resident care sub-areas, etc.), to the question level in block 424 (e.g., to be able to compare how certain questions are answered among different residents or at different times, to compare among related questions addressing similar areas of potential concern, etc.), to the individual level in block 428 (e.g., to be able to compare assessment results among individual residents, among individual staff members, among individual family members of residents, etc.), and or any other types of useful drill down.

For example, a facility assessment results in a low quality score for the "choices" care area. Drilling down to the resident care sub-area, facility section, question, and individual levels reveals that the lowest scores seem to come from residents on the third floor complaining that evening activities do not meet their interests. A quick follow-up with those residents further reveals that many of them enjoy the card game, Bridge, and some others are eager to learn. It may be desirable in that case for the resident care facility to simply add Bridge to its list of evening activities. It is worth noting that the ability to drill down to different levels of the data may allow for more efficient and effective resource allocations in many instances.

It will be appreciated that many other types of drill downs are possible, including drilling down to other categories of data, groups of categories, hierarchies and/or sorts of categories, etc. It will be further appreciated that, after each drill down (or a series of drill downs), it may be desirable to regenerate certain assessment data. For example, as shown in FIG. 1, the drilled down data may be passed back to blocks 132, 136, 140, and/or 144 to regenerate one or more types of assessment data. It will be even further appreciated that some or all of the assessment data (e.g., the resource allocation determinations generated in block 136 and the reports generated in block 144) may be ultimately used to allocate resources in block 152.

Figure 5:
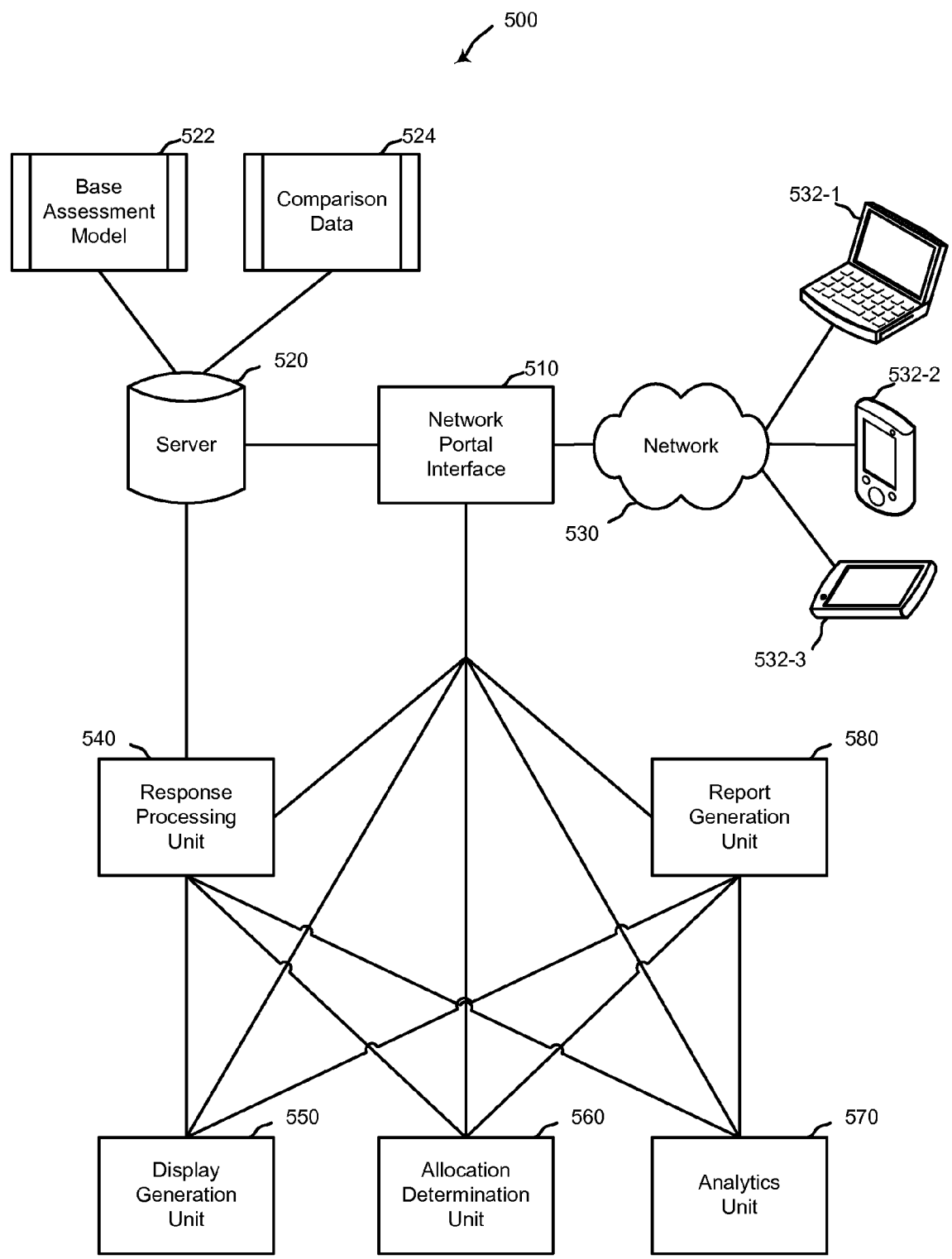
FIG. 5 shows a simplified block diagram of an illustrative system for determining resource allocations in resident care facilities, according to various embodiments of the invention.

Some embodiments of the invention are implemented in systems for allocating resources. In certain embodiments, the systems are operable to perform embodiments of the methods, like those described with reference to FIGS. 1-4. FIG. 5 shows a simplified block diagram of an illustrative system for determining resource allocations in resident care facilities, according to various embodiments of the invention.

The system 500 includes a network portal interface 510, operable to provide one or more assessor clients 532 with access to assessment data and functionality via a network 530. The assessor clients 532 may include any type of device or system operable to interface with the network 530 and the network portal interface 510. For example, an assessor client 532 may be include a laptop, a personal digital assistant ("PDA"), a cellular telephone, a tablet computer, etc. In some embodiments, the assessor client 532 logs in to the network portal interface 510 to gain access to the assessment data and/or functionality. For example, the assessor client 532 may transmit login data (e.g., a user name and password, biometrics, etc.) over the network 530 for authentication.

The network 530 may include any type of network operable to communicate data between the assessor clients 532 and the network portal interface 510. For example, the network 530 may include a local area network, a wide area network, the Internet, a cellular network, a wireless network, a fiber-optic network, a secure network (e.g., a virtual private network), or any other type of network known in the art. Further, in some embodiments, the network 530 includes data security functionality. In certain embodiments, the data security functionality includes secure network transmissions (e.g., network encryption, secure socket layer, etc.). In other embodiments, the data security functionality includes file-level security (e.g., file encryption, secure servers, password protection, etc.). In certain embodiments, the data security functionality is configured to provide data privacy and/or security as governed by a mandate. For example, the mandate may include a corporate mandate (e.g., a corporate privacy policy), a government mandate (e.g., the Health Insurance Portability and Accountability Act ("HIPAA"), the European Union Data Directive, etc.), etc.

Embodiments of the network portal interface 510 provide access to assessment data and assessment functionality. In some embodiments, the assessment data includes a base assessment model 522 and comparison data 524. In certain embodiments, the assessment data is stored on one or more servers 520, accessible to the network portal interface 510 (e.g., directly, over a network, etc.). The one or more servers 520 may include secure servers, networked servers, flat-file or relational databases, and/or any other useful data storage and access functionality. In some embodiments, the servers 520 are local to the facility performing the assessment, while in other embodiments, the servers 520 are remote. For example, a resident care facility may store its comparison data 524 and part of its base assessment model 522 on a local computer in an on-site management office, while the remainder of the base assessment model 522 is stored in a central government server.

The base assessment model 522 may include information from which an assessment (e.g., assessment questions and formats) may be derived, in some cases according to a government or predefined assessment program. In one embodiment, the base assessment model 522 includes the QIS, and/or information relating to the QIS. In certain embodiments, resident care facilities and/or other entities may add information to the base assessment model 522 to influence future assessments.

The comparison data 524 may include information from other assessment models, information from past assessments, information relating to previous assessments and/or citations, or any other useful information for comparing the results of an assessment or otherwise affecting the value of the results. For example, the comparison data 524 may provide baseline or normalization information for the quality score calculation, or additional data to make the calculation more precise or useful. In certain embodiments, the comparison data 524 is derived from the base assessment model 522, while in other embodiments, the comparison data 524 is derived from another source of stored data. In various embodiments, the comparison data 524 may include assessment results and/or datasets from past assessments of the same or a different resident care facility, the same or a different sample or geographic location within a resident care facility, the same or a different assessor, etc.

In some embodiments, the network portal interface 510 provides assessment-related functionality through one or more functional units. These functional units may, individually or collectively, be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

One such functional unit that is included in embodiments of the system 500 is a response processing unit 540. The response processing unit 540 may be operable to receive sets of assessment responses and process them, for example, to generate one or more assessment datasets. The assessment datasets may include processed versions of the assessment results (e.g., the answers to the assessment questions in a relational database, etc.), information relating to the assessment (e.g., time information, assessor information, facility information, file information, etc.), or any other useful information.

Embodiments of the response processing unit 540 may be operable to generate relational and/or flat-file databases of assessment responses, audit assessment data (e.g., determine whether the data is in a proper format, whether some or all of the questions have been answered, whether the data has been properly stored and/or uploaded to a server, evaluate whether certain assessment data goals have been met, etc.), etc. In some embodiments, the response processing unit 540 is operable to generate one or more quality scores, in some cases relating to a resident care area, a resident care sub-area, or some combination thereof.

The response processing unit 540 and/or the network portal interface 510 may be in communication with other functional units, including a display generation unit 550, an allocation determination unit 560, an analytics unit 570, and a report generation unit 580. Various embodiments of the display generation unit 550 are operable to generate and/or output displays of assessment-related information. For example, the display generation unit 550 may be configured to generate graphical displays of assessment data, quality scores, comparison data, base assessment model data, etc. Various embodiments of the allocation determination unit 560 are operable to determine resource allocations from assessment-related information. For example, the allocation determination unit 560 may be configured to determine the allocation of financial resources based on quality scores. Various embodiments of the analytics unit 570 are operable to perform analytics on assessment-related information. For example, the analytics unit 570 may be configured to perform various database analysis functions (e.g., sorting, filtering, parsing, etc.) or statistical processing functions (e.g., Bayesian analyses, correlations, line fitting, predictive algorithms, interpolation and extrapolation, etc.).

Various embodiments of the report generation unit 580 are operable to generate and/or output reports of assessment-related information. For example, the report generation unit 580 may be configured to report assessment data, quality scores, comparison data, base assessment model data, displays generated by the display generation unit 550, resource allocation determinations generated by the allocation determination unit 560, analytics generated by the analytics unit 570, etc. In some embodiments, the report generation unit 580 is operable to generate reports formatted for output as a file, for printing, for uploading to the Internet, or for any other useful type of reporting. Further, in certain embodiments, the report generation unit 580 is operable to provide functionality to drill down to various levels of data for viewing and/or reporting.

It will be appreciated that the various components of the system 500 may be implemented in a number of ways according to embodiments of the invention. In some embodiments, the blocks of the system 500 are implemented as separate hardware components or as functional blocks within one or more hardware components. In other embodiments, some or all of the functionality of the system 500 is implemented as computer-readable instructions stored on a computational medium, or as some other form of computational system.

Figure 6A:
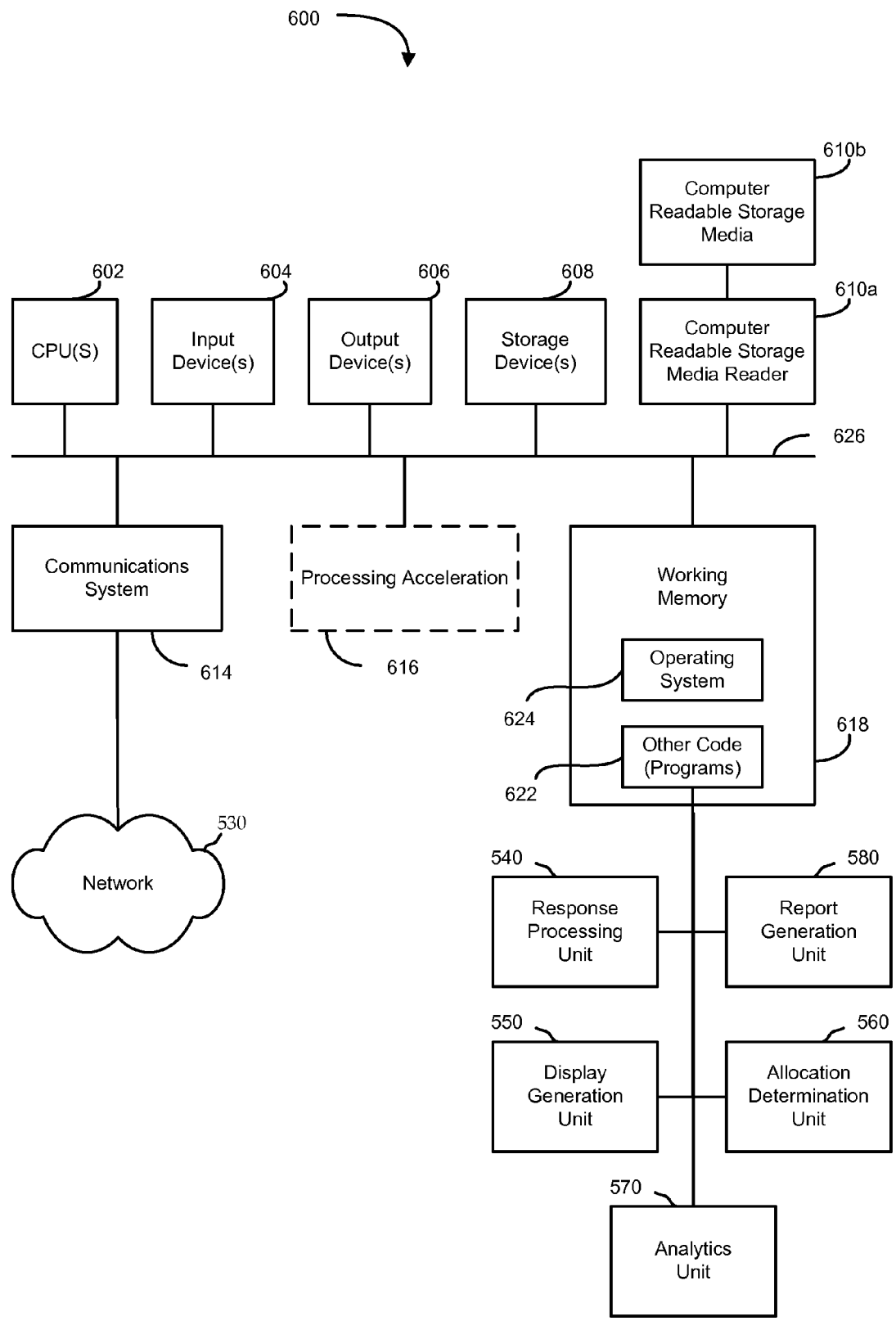
FIG. 6A shows an embodiment of a computational system for implementing a network interface portal, according to various embodiments of the invention.
Figure 6B:
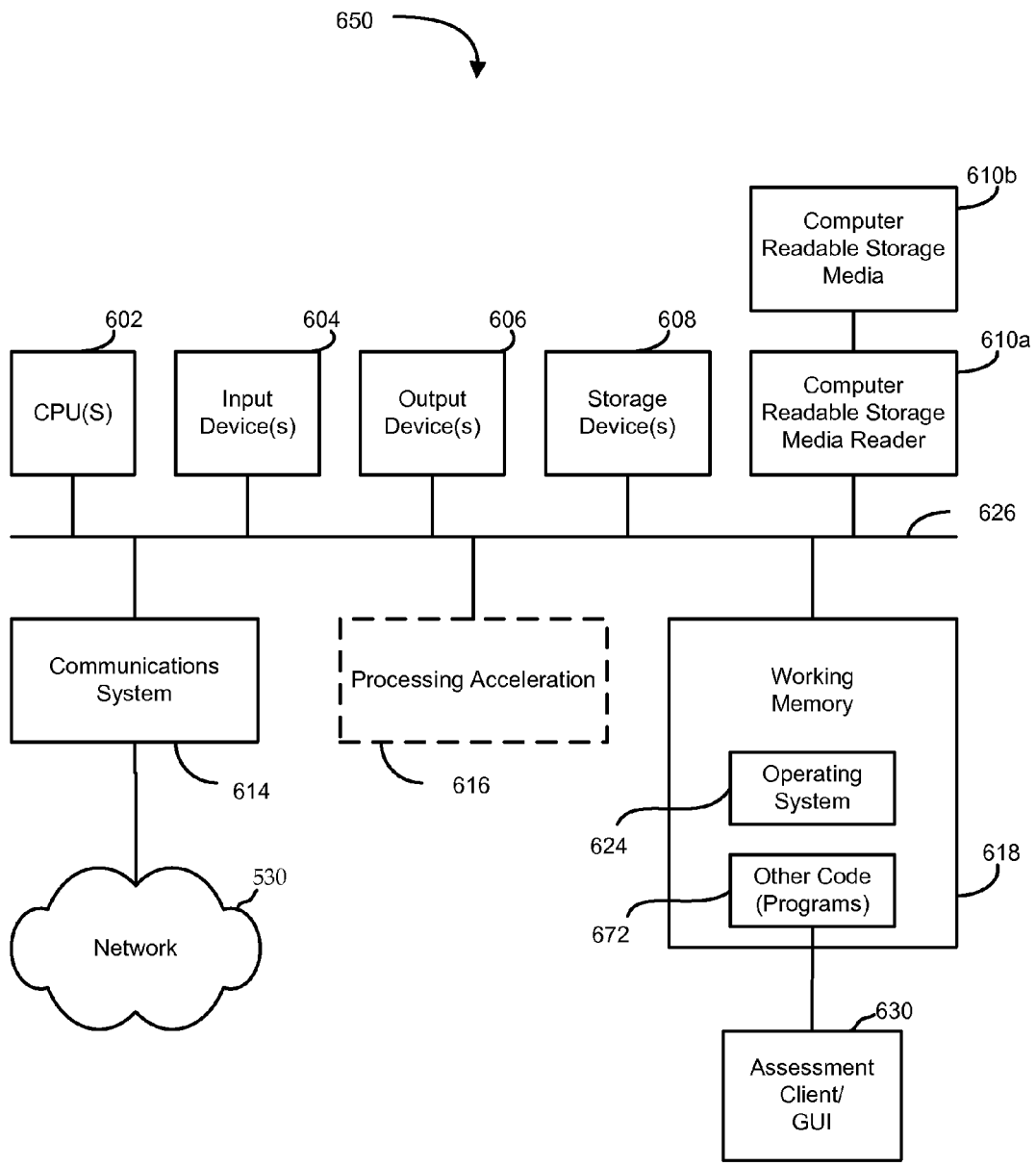
FIG. 6B shows an embodiment of a computational system for implementing an assessment client, according to various embodiments of the invention.

Illustrative computational systems for implementing embodiments of the invention are shown in FIGS. 6A and 6B, respectively. It should be noted that FIGS. 6A and 6B are meant only to provide generalized illustrations of various components, any or all of which may be utilized as appropriate. FIGS. 6A and 6B, therefore, broadly illustrate how individual system elements may be implemented in a relatively separated or relatively more integrated manner.

FIG. 6A shows an embodiment of a computational system for implementing a network interface portal, according to various embodiments of the invention. In some embodiments, the computational system 600 may be operable to implement the network interface portal 510 of FIG. 5. The computational system 600 is shown having hardware elements that may be electrically coupled via a bus 626 (or may otherwise be in communication, as appropriate). The hardware elements may include one or more processors 602, including without limitation one or more general-purpose processors and/or one or more special-purpose processors (such as digital signal processing chips, graphics acceleration chips, and/or the like); one or more input devices 604, which can include without limitation a mouse, a keyboard, and/or the like; and one or more output devices 606, which can include without limitation a display device, a printer, and/or the like.

The computational system 600 may further include (and/or be in communication with) one or more storage devices 608, which can comprise, without limitation, local and/or network accessible storage and/or can include, without limitation, a disk drive, a drive array, an optical storage device, a solid-state storage device such as a random access memory ("RAM"), and/or a read-only memory ("ROM"), which can be programmable, flash-updateable, and/or the like. The computational system 600 might also include a communications subsystem 614, which can include without limitation a modem, a network card (wireless or wired), an infra-red communication device, a wireless communication device and/or chipset (such as a Bluetooth device, an 802.11 device, a WiFi device, a WiMax device, cellular communication facilities, etc.), and/or the like. The communications subsystem 614 may permit data to be exchanged with a network (e.g., the network 530 of FIG. 5), and/or any other devices described herein. In many embodiments, the computational system 600 will further comprise a working memory 618, which can include a RAM or ROM device, as described above.

The computational system 600 also may include software elements, shown as being currently located within the working memory 618, including an operating system 624 and/or other code, such as one or more application programs 622, which may include computer programs of embodiments of the invention, and/or may be designed to implement methods of embodiments of the invention and/or configure systems of embodiments of the invention, as described herein. For example, the application programs 622 may include functionality to implement the response processing unit 540, the display generation unit 550, the allocation determination unit 560, the analytics unit 570, and/or the report generation unit 580 of FIG. 5.

Merely by way of example, one or more procedures described with respect to the method(s) discussed above might be implemented as code and/or instructions executable by a computer (and/or a processor within a computer). A set of these instructions and/or code might be stored on a computer readable storage medium 610b. In some embodiments, the computer readable storage medium 610b is the storage device(s) 608 described above. In other embodiments, the computer readable storage medium 610b might be incorporated within a computational system, such as the system 600. In still other embodiments, the computer readable storage medium 610b might be separate from the computational system (i.e., a removable medium, such as a compact disc, etc.), and/or provided in an installation package, such that the storage medium can be used to configure a general purpose computer with the instructions/code stored thereon. These instructions might take the form of executable code, which is executable by the computational system 600 and/or might take the form of source and/or installable code, which, upon compilation and/or installation on the computational system 600 (e.g., using any of a variety of generally available compilers, installation programs, compression/decompression utilities, etc.), then takes the form of executable code. In these embodiments, the computer readable storage medium 610b may be read by a computer readable storage media reader 610a.

In one embodiment, the invention employs a computational system (such as the computational system 600) to perform methods of embodiments of the invention. According to a set of embodiments, some or all of the procedures of such methods are performed by the computational system 600 in response to processor 602 executing one or more sequences of one or more instructions (which might be incorporated into the operating system 624 and/or other code, such as an application program 622) contained in the working memory 618. Such instructions may be read into the working memory 618 from another machine-readable medium, such as one or more of the storage device(s) 608 (or 610). Merely by way of example, execution of the sequences of instructions contained in the working memory 618 might cause the processor(s) 602 to perform one or more procedures of the methods described herein. In this way, the computational system 600 can be "configured to" or "operable to" perform any number of such procedures or methods.

The terms "machine readable medium" and "computer readable medium," as used herein, refer to any medium that participates in providing data that causes a machine to operate in a specific fashion. In an embodiment implemented using the computational system 600, various machine-readable media might be involved in providing instructions/code to processor(s) 602 for execution and/or might be used to store and/or carry such instructions/code (e.g., as signals). In many implementations, a computer readable medium is a physical and/or tangible storage medium. Such a medium may take many forms, including but not limited to, non-volatile media, volatile media, and transmission media. Non-volatile media includes, for example, optical or magnetic disks, such as the storage device(s) (608 or 610). Volatile media includes, without limitation dynamic memory, such as the working memory 618. Transmission media includes coaxial cables, copper wire, and fiber optics, including the wires that comprise the bus 626, as well as the various components of the communication subsystem 614 (and/or the media by which the communications subsystem 614 provides communication with other devices). Hence, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punchcards, papertape, any other physical medium with patterns of holes, a RAM, a PROM, an EPROM, a FLASH-EPROM, any other memory chip or cartridge, a carrier wave as described hereinafter, or any other medium from which a computer can read instructions and/or code.

Various forms of machine-readable media may be involved in carrying one or more sequences of one or more instructions to the processor(s) 602 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computational system 600. These signals, which might be in the form of electromagnetic signals, acoustic signals, optical signals, and/or the like, are all examples of carrier waves on which instructions can be encoded, in accordance with various embodiments of the invention.

The communications subsystem 614 (and/or components thereof) generally may receive the signals, and the bus 626 then may carry the signals (and/or the data, instructions, etc. carried by the signals) to the working memory 618, from which the processor(s) 602 may retrieve and execute the instructions. The instructions received by the working memory 618 may optionally be stored on a storage device 608 either before or after execution by the processor(s) 602.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

FIG. 6B shows an embodiment of a computational system for implementing an assessment client, according to various embodiments of the invention. In some embodiments, components of the client terminal 650 are similar to respective components of the computational system 600 of FIG. 6A. However, the client terminal 650 includes application programs 672 directed to implement functions of an assessment client (e.g., 532 of FIG. 5).

In certain embodiments, the application programs 672 provide interface functionality, operable to interface the client terminal 650 with a network interface portal. In other embodiments, the application programs 672 provide a graphical user interface through which a user of the client terminal 650 may interact with the client terminal 650. In one example, the user of the terminal is an assessor performing a facility assessment. In another example, the user of the terminal is a manager of a resident care facility, viewing and analyzing the results of one or more facility assessments.

It should be noted that the methods, systems, devices, and software discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

It should also be appreciated that the following systems, methods, and software may individually or collectively be components of a larger system, wherein other procedures may take precedence over or otherwise modify their application. Also, a number of steps may be required before, after, or concurrently with the following embodiments.

Specific details are given in the description to provide a thorough understanding of the embodiments. However, it will be understood by one of ordinary skill in the art that the embodiments may be practiced without these specific details. For example, well-known circuits, processes, algorithms, structures, waveforms, and techniques have been shown without unnecessary detail in order to avoid obscuring the embodiments. It will be further understood by one of ordinary skill in the art that the embodiments may be practiced differently in different environments. For example, one environment may include a wireless network providing substantially constant access to the Internet from an assessor terminal; while another environment may include no wireless connection and may be implemented with more local data storage and buffering capability.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the invention. Accordingly, the above description should not be taken as limiting the scope of the invention, as described in the following claims.

What is claimed is:

1. A system for generating resource allocation determinations for a nursing home facility, the system comprising:
   a computer operable to provide a base assessment model, modeled after a Quality Indicator Survey, wherein the Quality Indicator Survey comprises questions addressing a plurality of resident care areas, the plurality of resident care areas relating to at least one of choices, dignity, abuse, health, personal property, or quality;
   a network portal interface operable to provide a set of assessment questions to an assessor terminal, the set of assessment questions relating to at least a portion of the plurality of resident care areas comprised in the Quality Indicator Survey, wherein the assessor terminal is operable to:
provide the set of assessment questions to an assessor; and
receive responses to the set of assessment questions based on answers provided to the assessor by a number of respondents
a response processing unit in operative communication with the network portal interface and the computer and operable to:
generate quality scores for each of the plurality of resident care areas based on the responses; and
generate a likelihood of citation in each resident care area as a function of the respective quality scores, the number of respondents, a model threshold, and a model sample size, the model threshold and the model sample size being derived from the Quality Indicator Survey; and
a display generation unit in operative communication with the response processing unit and operable to display each likelihood of citation.

2. The system of claim 1, wherein the set of respondents comprises at least one of a resident of the nursing home facility, a relative of the resident of the nursing home facility, or an employee of the nursing home facility.

3. The system of claim 1, wherein the display generation unit is further operable to display each quality score graphically in relation to its resident care area.

4. The system of claim 3, wherein the display generation unit is operable to display each quality score graphically in relation to its resident care area by:
displaying a first data range in relation to a graphical scale, the first data range representing a range of scores in the resident care area indicative of a substantial certainty of citation in the resident care area;
displaying a second data range in relation to the graphical scale, the second data range representing a range of scores in the resident care area indicative of an uncertain likelihood of citation in the resident care area;
displaying a third data range in relation to the graphical scale, the third data range representing a range of scores in the resident care area indicative of a substantial certainty of no citation in the resident care area; and
displaying an indicator indicating a location of the quality score in relation to the graphical scale.

5. The system of claim 1, further comprising:
an allocation determination unit, in operative communication with the response processing unit, and operable to formulate a resource allocation determination as a function of at least one of the quality scores.

6. The system of claim 1, further comprising:
an allocation determination unit, in operative communication with the response processing unit, and operable to formulate a resource allocation determination as a function of at least one of the likelihoods of citation.

7. A method for generating information for determining resource allocation in a resident care facility, the method comprising:
providing a set of assessment questions to an assessor, the set of assessment questions being:
based on a base assessment model having questions relating to a plurality of resident care areas; and
related to at least a portion of the plurality of resident care areas;
receiving responses to at least a portion of the set of assessment questions from a number of respondents;
processing the responses to generate an assessment dataset;
generating, with a computer, a quality score for at least one of the resident care areas based on the assessment dataset;
generating, with a computer, a likelihood of citation in the resident care area associated with the quality score, as a function of the quality score, the number of respondents, a model threshold, and a model sample size, the model threshold and the model sample size being derived from the base assessment model; and
displaying the likelihood of citation for the resident care area associated with the quality score.

8. The method of claim 7, further comprising:
providing a computer network portal interface, the computer network portal interface being stored on a server and operable to interface with an assessor client terminal, wherein:
providing the set of assessment questions comprises providing the set of assessment questions via the computer network portal interface to the assessor client terminal, and
receiving the responses comprises receiving the responses via the computer network portal interface from the assessor client terminal.

9. The method of claim 7, further comprising:
generating data ranges associated with the quality score as a function of the data derived from the base assessment model, wherein:
a first data range represents a range of possible quality scores in the resident care area with a substantially high likelihood of citation in the resident care area;
a second data range represents a range of possible quality scores in the resident care area with a substantially uncertain likelihood of citation in the resident care area; and
a third data range represents a range of possible quality scores in the resident care area with a substantially low likelihood of citation in the resident care area.

10. The method of claim 9, wherein displaying the quality score comprises:
displaying a graphical scale indicating a full range of possible quality scores for the resident care area;
displaying the first data range in relation to the graphical scale;
displaying the second data range in relation to the graphical scale;
displaying the third data range in relation to the graphical scale; and
displaying an indicator indicating the location of the quality score in relation to the graphical scale.

11. The method of claim 7, further comprising wherein generating a likelihood of citation in the resident care area associated with the quality score comprises:
calculating a positive predictive value of the quality score resulting in a citation according to the base assessment model.

12. The method of claim 7, further comprising:
deriving a citation threshold from the base assessment model; and
converting the citation threshold to a first threshold quality score, such that, for the resident care area, the base assessment model indicates a substantially certain likelihood of citation when the generated quality score is below the first threshold quality score and the base assessment model indicates a substantial certainty of no likelihood of citation when the generated quality score is above the first threshold quality score.

13. The method of claim 12, further comprising:
displaying a graphical scale indicating a full range of possible quality scores for the resident care area;
displaying a first data range in relation to the graphical scale, the first data range representing a range of the possible quality scores in the resident care area falling below the first threshold quality score;
displaying a second data range in relation to the graphical scale, the second data range representing a range of the possible quality scores in the resident care area falling above the first threshold quality score; and
displaying an indicator indicating the location of the generated quality score in relation to the graphical scale.

14. The method of claim 12, further comprising:
deriving a second threshold quality score greater than the first threshold quality score,
wherein the second threshold quality score indicates a quality score for the resident care area where there is a maximum positive difference between an upper score and a lower score,
wherein the upper score indicates a composite positive predictive value, according to the base assessment model, of a citation resulting from a range of the possible quality scores falling above the second threshold quality score, and
wherein the lower score indicates a composite positive predictive value, according to the base assessment model, of a citation resulting from a range of the possible quality scores falling below the second threshold quality score and above the first threshold quality score.

15. The method of claim 14, further comprising:
displaying a graphical scale indicating a full range of possible quality scores for the resident care area;
displaying a first data range in relation to the graphical scale, the first data range representing a range of the possible quality scores in the resident care area falling below the first threshold quality score;
displaying a second data range in relation to the graphical scale, the second data range representing a range of the possible quality scores in the resident care area falling above the first threshold quality score and below the second threshold quality score;
displaying a third data range in relation to the graphical scale, the third data range representing a range of the possible quality scores in the resident care area falling above the second threshold quality score; and
displaying an indicator indicating the location of the generated quality score in relation to the graphical scale.

16. The method of claim 7, further comprising:
providing a subsequent assessment question based on at least one of the set of responses.

17. The method of claim 7, further comprising:
hiding a subsequent assessment question based on at least one of the set of responses.

18. The method of claim 7, wherein at least a portion of the responses relate to personal observations made by the assessor.

19. The method of claim 7, wherein at least a portion of the set of responses relate to answers provided to the assessor by residents residing at the resident care facility.

20. The method of claim 7, wherein at least a portion of the set of responses relate to answers provided to the assessor by relatives of residents residing at the resident care facility.

21. The method of claim 7, wherein at least a portion of the set of responses relate to answers provided to the assessor by staff of the resident care facility.

22. The method of claim 7, wherein at least a portion of the set of responses relate to prior resident evaluation data.

23. The method of claim 7, further comprising:
generating a quality score for each of a set of care sub-areas,
wherein at least one of the plurality of care areas comprises the set of care sub-areas.

24. The method of claim 7, wherein the generated quality score for the at least one of the resident care areas is based in part on data relating to another of the resident care areas.

25. The method of claim 7, further comprising:
analyzing the assessment dataset to generate an analytic dataset.

26. The method of claim 7, further comprising:
refining the set of quality scores based on a set of comparison data.

27. The method of claim 7, further comprising:
refining the set of quality scores based on a set of previously-acquired assessment results.

28. The method of claim 7, wherein the citation comprises an initiation of a legal proceeding relating to a sub-standard practice of the resident care facility.

29. The method of claim 7, wherein the base assessment model comprises:
a predefined assessment dataset; and
a plurality of prior assessment datasets, each prior assessment dataset having been generated from responses to prior assessments.

30. The method of claim 29, wherein generating the quality score comprises:
generating the quality score as a function of the predefined assessment dataset; and
refining the quality score based on at least a portion of the prior assessment datasets.

31. The method of claim 7, further comprising:
formulating a resource allocation determination as a function of the likelihood of citation.

32. The method of claim 31, wherein the resource allocation determination is indicative of an allocation of resources operable to reduce the likelihood of citation in the resident care area associated with the quality score.

33. The method of claim 31, wherein the resource allocation determination is indicative of an allocation of resources among a plurality of resident care areas, resident care sub-areas, or resident care facilities.

34. The method of claim 7, further comprising:
encrypting the set of assessment data.

35. The method of claim 7, wherein:
the base assessment model comprises the Quality Indicator Survey;
the citation comprises a trigger for a Stage II investigation; and
the likelihood of citation comprises a likelihood that a further citation will be issued as a result of the Stage II investigation.

36. The method of claim 7, further comprising:
displaying the quality score graphically in relation to the data derived from the base assessment model.

37. A computer-readable storage medium having a computer-readable program embodied therein for directing operation of a computer interface, the computer-readable program including instructions for generating information for determining resource allocation in a resident care facility in accordance with the following:

providing a set of assessment questions to an assessor via the computer interface, the set of assessment questions being based on a base assessment model having questions relating to a plurality of resident care areas, and related to at least a portion of the plurality of resident care areas;

receiving, via the computer interface, responses to at least a portion of the set of assessment questions, at least a portion of the responses relating to answers provided to the assessor by a number of respondents;

processing the responses to generate an assessment dataset; and generating a quality score for at least one of the resident care areas based on the assessment dataset; and generating a likelihood of citation in the resident care area associated with the quality score as a function of the quality score, the number of respondents, a model threshold, and a model sample size, the model threshold and the model sample size being derived from the base assessment model.

38. The computer-readable storage medium of claim 37, wherein the instructions for generating information for determining resource allocation in the resident care facility are further in accordance with providing a computer network portal interface operable to interface with an assessor client terminal.

39. The computer-readable storage medium of claim 37, wherein the instructions for generating information for determining resource allocation in the resident care facility are further in accordance with displaying the quality score graphically in relation to the data derived from the base assessment model.

40. The computer-readable storage medium of claim 37, wherein the instructions for generating information for determining resource allocation in the resident care facility are further in accordance with analyzing the assessment dataset to generate an analytic dataset.

41. The computer-readable storage medium of claim 37, wherein the instructions for generating information for determining resource allocation in the resident care facility are further in accordance with formulating a resource allocation determination as a function of the quality score.

42. The computer-readable storage medium of claim 37, wherein the instructions for generating information for determining resource allocation in the resident care facility are further in accordance with displaying the likelihood of citation for the resident care area associated with the quality score.

* * * * *